US007419640B2

(12) United States Patent
Suri et al.

(10) Patent No.: US 7,419,640 B2
(45) Date of Patent: Sep. 2, 2008

(54) MICROPOROUS FILTRATION BASED DOT IMMUNOASSAY DEVICE FOR METHOD FOR SCREENING OF ANALYTES AND METHOD OF USE

(75) Inventors: Chander Raman Suri, Chandigarh (IN); Manoj Raje, Chandigarh (IN); Grish Chandra Varshney, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 145 days.

(21) Appl. No.: 10/393,404

(22) Filed: Mar. 20, 2003

(65) Prior Publication Data

US 2004/0185577 A1    Sep. 23, 2004

(51) Int. Cl.
*B01L 11/00* (2006.01)
(52) U.S. Cl. .................... 422/101; 422/99; 422/100; 435/6; 436/180
(58) Field of Classification Search ........... 422/99–101; 436/177, 180; 435/39, 6
See application file for complete search history.

(56) References Cited

U.S. PATENT DOCUMENTS

| 4,675,299 | A | | 6/1987 | Witty et al. ................. 436/165 |
| 4,913,791 | A | | 4/1990 | Hurd et al. ............... 204/299 R |
| 5,210,077 | A | * | 5/1993 | Brandon et al. ......... 530/388.21 |
| 5,219,528 | A | * | 6/1993 | Clark .......................... 422/101 |
| 5,503,741 | A | | 4/1996 | Clark .......................... 210/232 |
| 6,593,085 | B1 | * | 7/2003 | Barnett et al. .................. 435/6 |
| 2003/0116497 | A1 | * | 6/2003 | Carlson et al. .............. 210/435 |

FOREIGN PATENT DOCUMENTS

EP    0 439 017    7/1991

OTHER PUBLICATIONS

Ijsselmuiden, O.E. et al. "Optimizing the solid-phasxe immunofiltration assay; A rapid alternative to immunoassays", *J. Of Immunological Methods*, 119 (1989) 35-43.

* cited by examiner

*Primary Examiner*—Jill Warden
*Assistant Examiner*—Jyoti Nagpaul
(74) *Attorney, Agent, or Firm*—Ladas & Parry LLP

(57) ABSTRACT

The present invention is based on rapid displacement of solvents under mild vacuum in solution-solid phase reaction of immunocomplex [Ijsselmuiden et al., J. Immunol. Methods, 6 (1989): 35]. In the present invention, this is achieved by a microporous absorbing pad upon which a nitrocellulose transfer membrane is placed. The absorbing pad under mild vacuum generated/regulated by running tap effectively filters out the unbound ligand and rinsing solutions through transfer membrane, thus enhancing the reaction kinetics of immunocomplex. This mechanism, in turn reduces the incubation steps of antibody-antigen reaction from hours to few minutes, allowing total assay time in less than 20 minutes.

18 Claims, 1 Drawing Sheet

Figure 1:
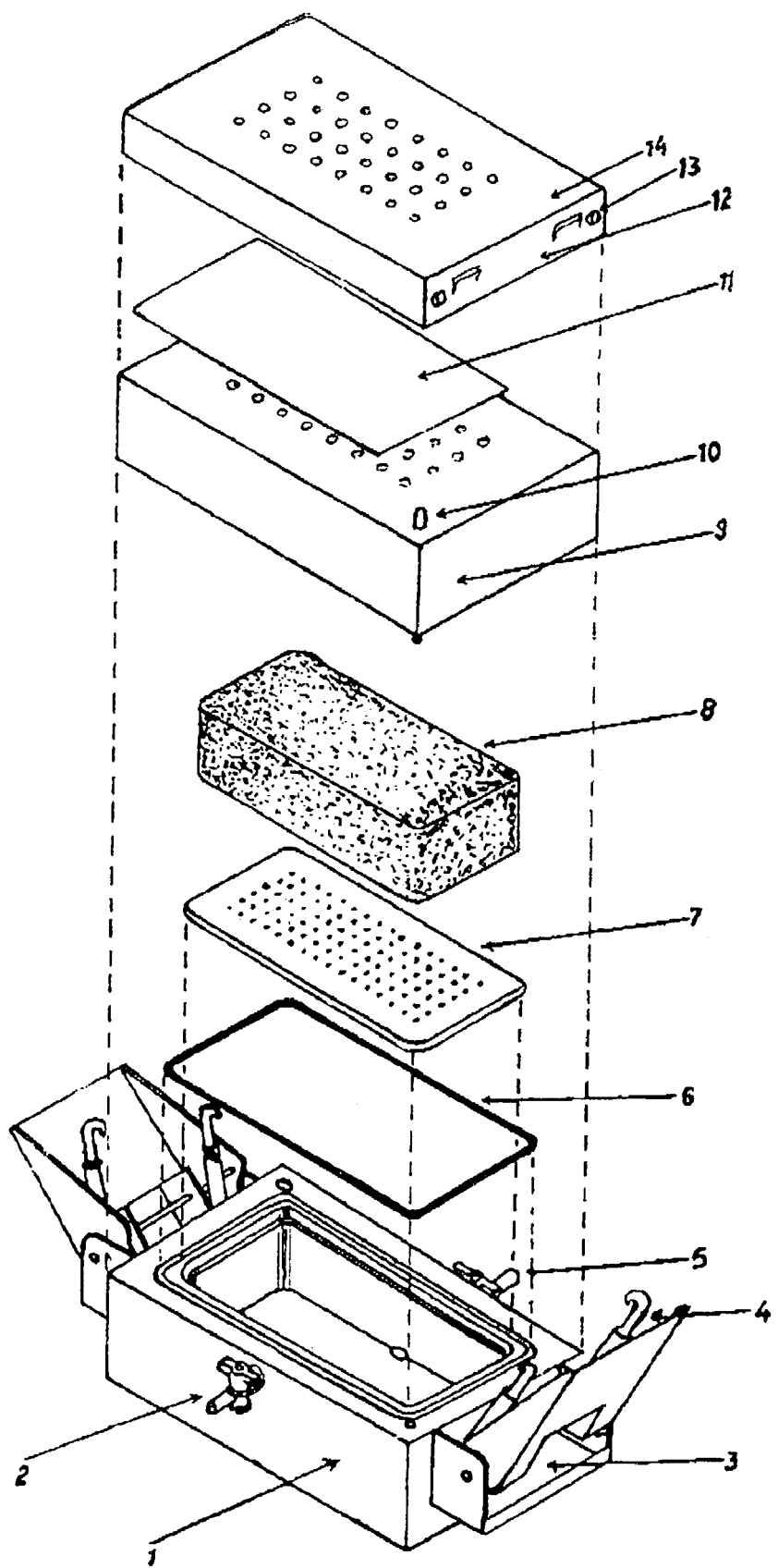

MICROPOROUS FILTRATION BASED DOT IMMUNOASSAY DEVICE FOR METHOD FOR SCREENING OF ANALYTES AND METHOD OF USE

FIELD OF THE INVENTION

The present invention relates to an efficient and improved device for the screening of analytes using a microporous filtration based dot immunoassay method. More particularly this invention is based on the rapid solvent displacement method using a microporous pad. The invention is applicable for rapid screening of samples such as pesticides, hormones, and proteins with the ability of testing multiple samples in a single run. The device can be used for testing in all types of field conditions as it is extremely handy, versatile, efficient, self contained, ands meets with the prime objective of this invention to develop an improved dot blot method for rapid immunoscreening of substances in samples with the ability of testing multiple samples in a single run.

BACKGROUND OF THE INVENTION

In prior art immunofiltration system developed by Pierce Corporation, USA wherein its Easy-Titer Enzyme linked immunofiltration assay kit (Immunofiltration Apparatus, Pierce catalogue, page: 0-186) the solvent displacement is achieved by electrically operated vacuum pump. This makes it non-usable in remote locations having no access to electricity.

OBJECTS OF THE INVENTION

The main objective of the present invention is to have a device for screening of analytes using a microporous filtration based dot immunoassay method.

Another objective of the present invention is to make this device efficient, effective, handy and operable in all kinds of field conditions.

SUMMARY OF THE INVENTION

The principle of the present invention is based on rapid displacement of solvents under mild vacuum in solution-solid phase reaction of immunocomplex [Ijsselmuiden et al., J. Immunol. Methods, 6 (1989): 35]. In the present invention, this is achieved by a microporous absorbing pad upon which a nitrocellulose transfer membrane is placed. The absorbing pad under mild vacuum generated/regulated by running tap effectively filters out the unbound ligand and rinsing solutions through transfer membrane, thus enhancing the reaction kinetics of immunocomplex. This mechanism, in turn reduces the incubation steps of antibody-antigen reaction from hours to few minutes, allowing total assay time in less than 20 minutes.

Accordingly the present invention provides a microporous filtration based dot immunoassay device for screening of analytes, said device comprising three independent housings comprising of two upper housings and one lower housing, a transfer membrane, a microporous pad sandwiched between two upper housings, a polymer mesh placed over the lower housing, a seal means.

In one embodiment of the invention, the three housings comprise of one piece acrylic polymer sheet.

In another embodiment of the invention, wherein the transfer membrane is a nitrocellulose sheet.

In another embodiment of the invention, the absorbing pad is a high density polymeric sponge.

In another embodiment of the invention, the two upper housings have 32 holes each corresponding exactly to each other and all three housings are connected firmly through external connecting means.

In another embodiment of the invention, the seal means is an O ring.

In another embodiment of the invention, the analyte comprises of small molecules selected from small molecules of pesticides, proteins and hormones.

The present invention also relates to a method for microporous filtration dot immunoassay using a device comprising comprising three independent housings comprising of two upper housings and one lower housing, a transfer membrane, a microporous pad sandwiched between two upper housings, a polymer mesh placed over the lower housing, a seal means, said method comprising immobilizing a complimentary ligand to the analyte sample on the polymer mesh, adding a tracer along with the sample to each well, and then adding a substrate thereto, the enzyme tracer bound to membrane being converted to a colored product by a substrate and thereby functioning as an indicator of the proportion of the micromolecule in the sample.

In one embodiment of the invention, the color reaction of the tracer is stopped by means of a vacuum.

In another embodiment of the invention, the vacuum is generated through a running water tap.

In another embodiment of the invention, the analyte comprises small molecules selected from pesticides, hormones and proteins.

Accordingly, the present invention relates to a device for the screening of molecules using a microporous filtration based dot immunoassay method; such device being capable to screen multiple samples in a single run.

BRIEF DESCRIPTION OF THE ACCOMPANYING DRAWING

The FIGURE of the drawing is a schematic representation of the device of the invention.

DETAILED DESCRIPTION OF THE INVENTION

The features and advantages of the invention will be more apparent from the following more particular description of the device, as illustrated in the accompanying drawing. The drawing is not necessarily to the scale, emphasis instead being placed upon illustrating the principles of the invention.

In this screening device the nitrocellulose membrane contains the bound complimentary ligand (anti-pesticide antibody) immobilized on it. The sample containing pesticide competes with an enzyme bound pesticide derivative (tracer) for the available antibody binding sites. The more the pesticide concentration in a sample, the less enzyme tracer available for antibody binding sites. The enzyme tracer bound to membrane is converted to a colored product by a substrate. The developed color is an indicator, which is inversely proportional to pesticide concentration in the sample.

The screening device consists of three separate housings (1, 9 and 12) each made of one-piece acrylic polymer (Perspex) sheet as shown in FIG. 1. The transfer membrane (11) placed over the microporous pad (8) is sandwiched between the upper and the middle housings (9 and 12). The microporous pad is supported on a perspex mesh (7), which is placed over the lower housing (1) sealed via a silicon ring (6). The upper housing (12) contains 32 holes with silicon O-rings at bottom for blocking sample leakage. All three housings are held together via guided pins (10) and spring-loaded clamps (3, 4). The vacuum generated and regulated from running tap is connected to main system via vacuum line (2).

The other advantage of this device, unlike the existing method, is effective displacement of unbound ligand uniformly throughout the membrane surface by putting a microporous absorbing pad under the transfer membrane. The process of the present invention, hereby makes it very handy, portable, and does not require any power connection. It generates vacuum through running water, and only a few reagents are required for color development, and therefore most appropriate for every possible field application.

A further description of the invention is given in example below, which should not however be construed to limit the scope of the present invention unless otherwise stated.

EXAMPLE 1

Screening of Smaller Pesticide Molecules (2.4-dichlorophenoxyacetic acid

The nitrocellulose transfer membrane placed between upper two Perspex housings is spotted with 10 µl of anti-2, 4-D antibody solution made in phosphate buffer saline (150 mM, pH 7.4)) in each well. The membrane is kept for incubation for 5 minutes, and dried under the mild vacuum (~0.25 kg/cm$^2$). 100 µl PBS containing 0.5% Tween 20 (PBST) is then added to each well under same vacuum for removing unbound antibody molecules from membrane. The different concentrations of pesticide sample (1 ppb to 1 ppm) mixed with the enzyme tracer (pesticide-HRP) are added to each well and rinsed under mild vacuum. After rinsing again with PBST, the substrate (tetramethylbenzidine/H$_2$O$_2$) is added into each well to generate the color. The color reaction is stopped with water, which is then rinsed under mild vacuum. The intensity of color developed, inversely proportional to pesticide concentration in samples, is semi-quantified by comparing with standard test strip.

EXAMPLE 2

Screening of Protein Molecules, Serum Albumin in Samples

The nitrocellulose transfer membrane is spotted with 10µl of anti-BSA (bovine serum albumin) antibody solution made in phosphate buffer saline (PBS) in each well, kept for incubation for 5 minutes, and dried under the mild vacuum (~0.25 kg/cm$^2$). 100 µl PBS containing 0.5% Tween 20 (PBST) is then added to each well under same vacuum for removing unbound antibody molecules from membrane. The different concentrations of BSA (1 ng/ml to 1 µg/ml) made in phosphate buffer are added to each well and rinsed under mild vacuum. After rinsing with PBST, the second antibody (goat-anti-BSA) labelled with HRP (1:20,000 dilution) was added into each well. After rinsing again with PBST, substrate (tetramethylbenzidine/H$_2$O$_2$) is added into each well. The color reaction is stopped with water, which is then rinsed under mild vacuum. The intensity of color developed, directly proportional to pesticide concentration is semi-quantified with a standard test strip.

We claim:

1. An immunoassay device for screening an analyte in a liquid sample, comprising first and second upper housings and a lower housing, each of said first and second upper housings comprising holes for permitting the liquid sample to pass therethrough, transfer membrane means for binding a ligand, said transfer membrane means being sandwiched between the first and second upper housings and supported on the second upper housing, absorbing means disposed directly beneath the second upper housing for absorbing unbound ligand and solutions from the transfer membrane means, mesh means disposed on the lower housing for supporting said absorbing means, seal means for sealing the device, connecting means for connecting the first and second upper housings and the lower housing, and means for generating a vacuum in the device, said means for generating a vacuum comprising a water tap, wherein the device consists of the first and second upper and lower housings, the transfer membrane means, the absorbing means, the seal means, the vacuum means and the connecting means.

2. The device as claimed in claim 1, wherein each of the first and second upper housings and the lower housing comprises a one piece acrylic polymer sheet.

3. The device as claimed in claim 1, wherein the transfer membrane means comprises a nitrocellulose membrane.

4. The device as claimed in claim 1, wherein the absorbing means comprises a polymeric sponge.

5. The device as claimed in claim 1, wherein each of the first and second upper housings comprises 32 holes with the 32 holes in the first upper housing being axially aligned with the 32 holes in the second upper housing.

6. The device as claimed in claim 1, wherein the seal means comprises an O ring.

7. A kit comprising the device as claimed in claim 1 and a liquid sample comprising an analyte, the analyte comprising small molecules of a pesticide, protein or hormone.

8. A method for microporous filtration of a liquid sample comprising an analyte, said method comprising:
    (a) providing the device of claim 1;
    (b) introducing a solution comprising a ligand through the holes of the first upper housing to cause a portion of the ligand to be immobilized on the transfer membrane means, said ligand being complementary to the analyte such that the analyte can bind to the immobilized ligand;
    (c) introducing an enzyme tracer along with the liquid sample through the holes in the first upper housing, said tracer being bindable to the ligand such that the tracer and the analyte in the liquid sample compete for binding to the ligand;
    (d) introducing through the holes in the first upper housing a substrate that causes the tracer bound to the ligand immobilized on the transfer membrane means to change color such that the amount of the tracer bound to the ligand can be determined based on the intensity of the color.

9. The method as claimed in claim 8, comprising stopping the color change of the tracer by means of a vacuum.

10. The method as claimed in claim 9, wherein the vacuum is generated by running water through a tap.

11. The method as claimed in claim 10, wherein the analyte comprises small molecules of a pesticide, a hormone or a protein.

12. The method as claimed in claim 8, wherein the analyte comprises small molecules of a pesticide.

13. An immunoassay device for screening an analyte in a liquid sample comprising the analyte and a solvent, said device consisting of (a) first and second upper housings and a lower housing, each of said first and second upper housings comprising holes for permitting the liquid sample to pass therethrough, (b) transfer membrane means for binding the analyte and a ligand that is complementary to the analyte so as form an immunocomplex and for allowing the solvent to pass therethrough, said transfer membrane means being sandwiched between the first and second upper housings and supported on the second upper housing, (c) displacement means for displacement of the solvent that enhances a rate of forming the immunocomplex, the displacement means comprising absorbing means disposed beneath the transfer membrane means for absorbing unbound ligand and the solvent from the transfer membrane means, (d) mesh means disposed on the lower housing for supporting said absorbing means, and (e) seal means for sealing the device.

14. The device as claimed in claim 13, wherein each of the first and second upper housings and the lower housing comprises a one piece acrylic polymer sheet.

15. The device as claimed in claim 13, wherein the transfer membrane means comprises a nitrocellulose membrane.

16. The device as claimed in claim 13, wherein the absorbing means comprises a polymeric sponge.

17. The device as claimed in claim 13, wherein the displacement means comprises vacuum means for generating a vacuum in the device, said vacuum means comprising a water tap.

18. A method for microporous filtration of a liquid sample comprising an analyte, said method comprising:
  (a) providing the device of claim 13;
  (b) introducing a solution comprising a ligand through the holes of the first upper housing to cause a portion of the ligand to be immobilized on the transfer membrane means, said ligand being complementary to the analyte such that the analyte can bind to the immobilized ligand;
  (c) introducing an enzyme tracer along with the liquid sample through the holes in the first upper housing, said tracer being bindable to the ligand such that the tracer and the analyte in the liquid sample compete for binding to the ligand;
  (d) introducing through the holes in the first upper housing a substrate that causes the tracer bound to the ligand immobilized on the transfer membrane means to change color such that the amount of the tracer bound to the ligand can be determined based on the intensity of the color.

* * * * *